United States Patent [19]

Cardinal

[11] Patent Number: 4,601,893
[45] Date of Patent: Jul. 22, 1986

[54] LAMINATE DEVICE FOR CONTROLLED AND PROLONGED RELEASE OF SUBSTANCES TO AN AMBIENT ENVIRONMENT AND METHOD OF USE

[75] Inventor: John R. Cardinal, Old Lyme, Conn.

[73] Assignee: Pfizer Inc., New York, N.Y.

[21] Appl. No.: 678,722

[22] Filed: Dec. 6, 1984

Related U.S. Application Data

[63] Continuation-in-part of Ser. No. 577,950, Feb. 8, 1984, abandoned.

[51] Int. Cl.⁴ .......................... A61K 9/20; A61K 9/24
[52] U.S. Cl. .......................................... 424/15; 424/16; 424/19; 424/21; 604/890; 604/892
[58] Field of Search ............... 424/DIG. 7, 15, 16, 424/19, 21; 604/890, 892

[56] References Cited

U.S. PATENT DOCUMENTS

| | | | |
|---|---|---|---|
| 3,113,076 | 12/1963 | Jacobs | 167/82 |
| 3,844,285 | 10/1974 | Laby | 604/892 |
| 3,924,622 | 12/1975 | Brooke | 604/892 |
| 3,926,188 | 12/1975 | Baker et al. | 424/19 |
| 4,196,187 | 4/1980 | Dannelly et al. | 424/19 |
| 4,217,898 | 8/1980 | Theeuwes | 128/260 |
| 4,228,149 | 10/1980 | Brewer et al. | 424/14 |
| 4,357,312 | 11/1982 | Hsieh et al. | 424/19 |
| 4,381,780 | 5/1983 | Holloway | 604/892 |
| 4,483,846 | 11/1984 | Koide et al. | 604/892 |

FOREIGN PATENT DOCUMENTS

| | | | |
|---|---|---|---|
| 21758 | 1/1981 | European Pat. Off. | |
| 8200094 | 1/1982 | PCT Int'l Appl. | 604/892 |

OTHER PUBLICATIONS

Rhine et al., A.I.Ch.E. Symp. Ser. 77, 10-20 (1981).
Rhine et al., "Controlled Release of Bioactive Materials," R. Baker, ed., Academic Press, pp. 177-187 (1980).

Primary Examiner—John F. Niebling
Assistant Examiner—Terryence Chapman
Attorney, Agent, or Firm—Charles J. Knuth; Albert E. Frost; Peter C. Richardson

[57] ABSTRACT

Laminate device for the controlled and prolonged release of at least one active agent to an ambient environment comprising at least one core sheet, said core sheet or sheets comprising said agent or agents in a polymer matrix, and, in a preferred embodiment, a porosity enhancing agent in admixture with said agent; said core sheet or sheets being alternately sandwiched or interposed between coextensive inert polymeric films substantially impermeable to said environment and to said agent or agents, said device being perforated by one or a plurality of macroholes extending through said sheets and said films. In a modification of said device the perimeter edge thereof is coated by an inert polymeric film substantially impermeable to said environment and to said agent or agents. Also included are methods for making such a device.

38 Claims, 7 Drawing Figures

LAMINATE DEVICE FOR CONTROLLED AND PROLONGED RELEASE OF SUBSTANCES TO AN AMBIENT ENVIRONMENT AND METHOD OF USE

CROSS-REFERENCE TO RELATED APPLICATION

This application is a continuation-in-part of application Ser. No. 577,950, filed Feb. 8, 1984, now abandoned.

BACKGROUND OF THE INVENTION

1. Field of the Invention

This invention relates to an improved device for the controlled and prolonged release of at least one active agent to an ambient environment, and to a method for making such a device. More particularly, it relates to a laminate device for the controlled and prolonged release of at least one active agent, including a physiologically active agent, to an ambient environment, said device comprising at least one core sheet, said core sheet comprising said agent or agents in a polymeric matrix, said core sheets being sandwiched between coextensive inert polymeric films substantially impermeable to said environment and to said agent or agents, said device having one or more macroholes extending through said film and said core sheet or sheets. It particularly relates to such a device wherein the perimeter edges thereof, especially the perimeter edges of said core sheet or sheets are coated by an inert polymeric film substantially impermeable to said environment and to said agent or agents.

2. Description of the Prior Art

Delivery systems and devices for controlled release of drugs; i.e., controlled release and sustained or prolonged release, are well known in the art. A variety of methods have been described in the literature, including the physiological modification of absorption or excretion, modification of the solvent, chemical modification of the drug, adsorption of drug on an insoluble carrier, use of suspensions and implantation pellets (Edkins, J. Pharm. Pharmacol., 11, 54T, 66T, 1959). Other methods include mixing the drug with a carrier such as waxes, oils, fats and soluble polymers which is gradually disintegrated by the environment, e.g., body fluids, resulting in release of the drug. Much attention has been directed to the reservoir type of device; i.e., a device in which a drug is encased within a polymeric container, with or without a solvent or carrier, which allows passage of drug from the reservoir.

A further type of drug delivery device is the monolithic type in which a drug is dispersed in a polymer and from which the drug is release by degradation of the polymer and/or by passage of drug through the polymer. Included within the monolith type devices are the laminated drug dispensers.

U.S. Pat. No. 3,926,188, issued Dec. 16, 1975, describes three layer sandwich-type laminate drug dispensers comprising a core lamina of a crystalline drug of low water solubility dispersed in a polymer matrix interposed between two outer laminae of a drug release rate controlling polymer. A rather complex correlation between relative permeabilities, thicknesses and exposed surface areas of the laminae must be satisfied in order to achieve an approximately constant rate of drug release. The core lamina may be a homogeneous and substantially imperforate polymeric material or it may be a microporous polymer matrix. Ethylene vinylacetate copolymer (EVA) is disclosed as representative of an imperforate polymer. It is disclosed that the release rates of said laminates are not as constant as the release rates of comparable prior art reservoir devices in which the core is not exposed to the environment.

A three layer sandwich-type laminate is also described in U.S. Pat. No. 4,228,149, issued Oct. 14, 1980. One such device comprises a water soluble drug dispersed in a sheet of water insoluble polymer, especially EVA, which sheet is coated on both surfaces with a film of EVA forming a sandwich-type device. Said films may include a water soluble and/or biodegradable filler which, when the device is placed in a liquid environment, gradually decompose forming pores or channels which serve to connect the outer films with the central lamina. It is disclosed that variations in the release properties of the device can be achieved by forming a hole or holes in the sheet. It is further disclosed, however, that best results are realized without such holes.

Cleave, J. Pharm. Pharmacol. 17, 698-702 (1965) presents a theoretical discussion of geometrical considerations concerning the design of uncoated tablets having a uniform rate of release. Tablets having from one to 4 holes are considered. Optimal design is concluded to reside in a two-hole tablet. A one-hole tablet is judged unable to deliver a uniform rate.

U.S. Pat. No. 3,851,648, issued Dec. 3, 1974, describes devices for controlled release of a diffusible solid comprising a container having a cavity which communicates with the exterior medium and through which the contained solid is dispensed.

U.S. Pat. No. 4,299,613, issued Nov. 10, 1981, describes controlled release plant nutrient dispensers comprising an admixture of a plant nutrient, a porosigen and a polymer matrix.

Controlled delivery systems consisting of a polymer impermeable to a fluid environment and to active agent contained within said polymer, said polymer in laminar arrangement with a polymer that forms a microporous structure in a fluid environment are described in U.S. Pat. No. 4,217,898, issued Aug. 19, 1980.

Medicament containing tablets comprising a medicated portion soluble in gastrointestinal fluids, which portion is surrounded by an inert portion said inert portion having one or more holes extending through one face of said inert portion into said medicated portion to permit passage of said medicated portion into the gastrointestinal fluids when such a device is in use, are disclosed in U.S. Pat. No. 3,146,149.

Slow-release veterinary preparations comprising a veterinary medicament contained in a matrix which in turn is enclosed in a plastic envelope sealed at its edges and provided with a number of randomly placed small holes to render it permeable to rumen fluids, thus permitting access of said fluids to the medicament contained within the matrix within the envelope, are made known in European Patent Application No. 21,758, published Jan. 7, 1981.

U.S. Pat. No. 4,144,317, issued Mar. 3, 1979, divulges laminated drug delivery devices comprising a drug dispersed in a solid matrix, said matrix enclosed within an EVA barrier; and devices wherein drug is laminated between EVA copolymer sheets. Essential to the construction and operation of said devices is the presence of at least one barrier or wall of EVA through which the drug will pass by diffusion.

Rhine et al., in "Controlled Release of Reactive Materials", R. Baker, Ed., Academic Press, p. 177, 1980 present a discussion of the effect of matrix geometry on the rate of release of a drug from a matrix device comprising an inwardly releasing hemisphere. They demonstrate that such a device can, after a short burst of drug, achieve essentially zero order release rate for the duration of release. For a device of such geometry, the outer diameter should be greater than three times the inner diameter. Also, Rhine et al., A. I. Ch. E. Symp. Ser. 77, 10-20 (1981), discuss the release characteristics of an inwardly releasing sectioned cylinder.

SUMMARY OF THE INVENTION

This invention relates to an improved device for the controlled release of at least one active agent, including a physiologically active agent, to an ambient environment, especially to an aqueous liquid-containing environment, over a prolonged period of time. More particularly it relates to such devices useful for the controlled release of said agent or agents to said environment, especially when said agent is a physiologically active substance, and especially when said environment is the rumeno-reticular sac of a ruminant animal, said agent being released over a prolonged period of time at a controlled physiologically acceptable rate. The devices comprise a laminate comprising at least one core sheet, said core sheet or sheets comprising said agent or agents in a polymeric matrix, said sheets being interposed or sandwiched between coextensive inert polymeric films substantially impermeable to said agent and to said environment to which the device is exposed. One or more macroperforations extend through said films and through the core sheet or sheets. Said perforations give rise to development of inwardly releasing cylinders when the devices are in use.

The amount of active agent released in vitro from such inwardly releasing cylinders can be described in terms of equations developed by Lipper et al., J. Pharm. Sci., 66, 163-164 (1977). For the case where the substance is released via diffusion within solvent filled pores or channels within the core matrix, the appropriate forms of the release equations are:

$$M_r = (\lambda^2 - n^2)\left[ L\pi\epsilon\rho - L\pi\epsilon C_S + \frac{L\pi\epsilon C_S}{2\left(\frac{h}{n}\frac{\epsilon}{\tau} + \ln\frac{\lambda}{n}\right)} \right] -$$

$$\frac{L\pi\epsilon C_S n^2}{\frac{h}{n}\frac{\epsilon}{\tau} + \ln\frac{\lambda}{n}} \ln\frac{\lambda}{n}$$

and $$t = \frac{\left(\frac{h}{n}\frac{\epsilon}{\tau} - \frac{1}{2}\right)(\lambda^2 - n^2)\rho\tau + \lambda^2\tau\rho\ln\frac{\lambda}{n}}{2DC_S\frac{\epsilon}{\tau}}$$

where
 $M_r$ = total amount released
 t = time
 $\lambda$ = radius of cylinder at receding agent boundary
 n = radius of macroperforation
 L = thickness of the core matrix
 $\epsilon$ = porosity of matrix
 $\tau$ = tortuosity of matrix $\rho$ = density of agent
 $C_S$ = solubility of agent in environment
 h = thickness of the environment boundary layer at the surface of the cylinder
 D = diffusion coefficient for agent in environment Those skilled in the art will recognize that this equation, with appropriate modifications, can be utilized to predict the release rate of active agent from any device, irrespective of the nature of the core material and the agent undergoing release. Examples of the various types of core matrices include: agent dissolved in polymer (dissolved matrix), agent dispersed in a polymer at a concentration which exceeds its saturation solubility in the core polymer (dispersed matrix) and agent dispersed in a polymer at a concentration sufficient to produce continuous solvent filled channels within the polymer matrix upon depletion of the drug (porous matrix). Each of these types are useful embodiments of this invention which, by appropriate choice of agent, polymer and device design, including hole pattern, achieve a given overall release pattern as a function of time.

In the above equations, the thickness of the outer laminae is immaterial. If all parameters are known, one can then determine the number of macroperforations needed to achieve a given release rate.

The values $\lambda$, $\epsilon$, $\tau$, $\rho$, D and H, if not known, are determined by procedures known to those skilled in the art. For example, the diffusion coefficient, D, is determined as described in Jost, "Diffusion in Solids, Liquids and Gases," Academic Press Inc., New York, Revised Edition, Ch. XI, 436-488 (1960). The tortuosity and porosity of the matrix can be determined by procedures described in Polymer Engineering and Science 11, 284-288 (1971) or by Desai et al., J. Pharm. Sci. 55, 1224 (1966).

The devices of this invention provide a simple and practical, essentially zero order release device, by reason of their having at least one interior-releasing cylindrical surface wherein the entire surface of the cylinder participates in the release process.

BRIEF DESCRIPTION OF THE DRAWINGS

The drawings are not drawn to scale but are merely set forth to illustrate various embodiments of the invention.

DETAILED DESCRIPTION OF THE DRAWINGS

Figure 1:
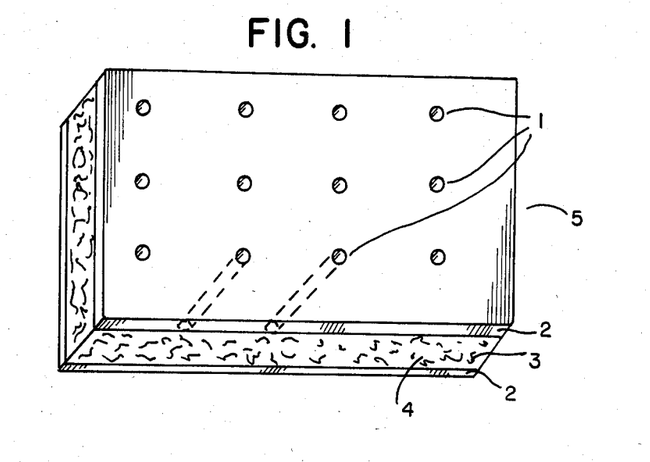
FIG. 1 is a perspective view of a three-layer (sandwich) laminate device, indicated by the number 5 of this invention, the edges of which are exposed.

FIGS. 1-5 illustrate various forms of the devices according to this invention. In FIG. 1, the device 5 comprises a three-layer laminate comprising a core lamina 3 of an impermeable polymer and two outer laminae 2, also of impermeable polymer. The core lamina, the edges of which are exposed, comprises drug 4 in impermeable polymer Macroperforations 1 extend through all laminae of the device.

Figure 2:
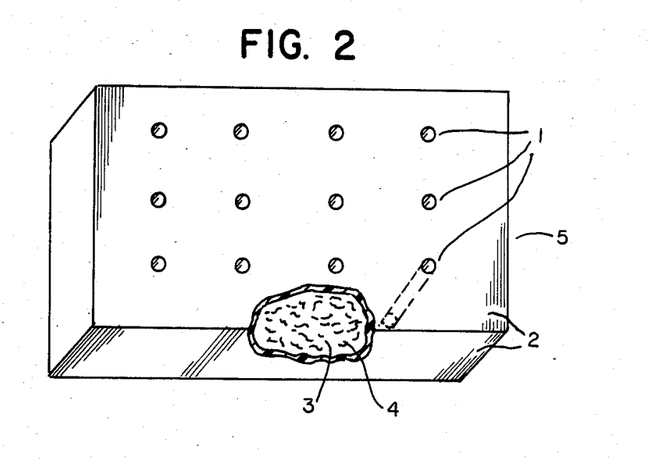
FIG. 2 is a perspective view of a laminate device 5 of this invention, the edges of which are coated. The cut away portion illustrates the active agent-carrying core sheet.

FIG. 2 shows a laminate device 5 in which the edge surfaces are covered by an impermeable polymer and having symmetrically placed macroperforations 1 which extend through the device.

Figure 3:
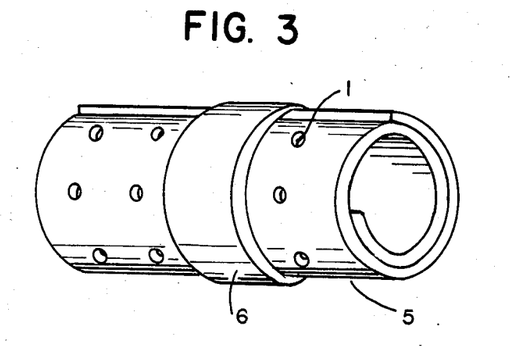
FIG. 3 is a perspective view of a device of FIG. 2 in the constrained configuration.

FIG. 3 shows a laminate device 5 of this invention constrained into cylindrical form by constraining means 6.

Figure 4:
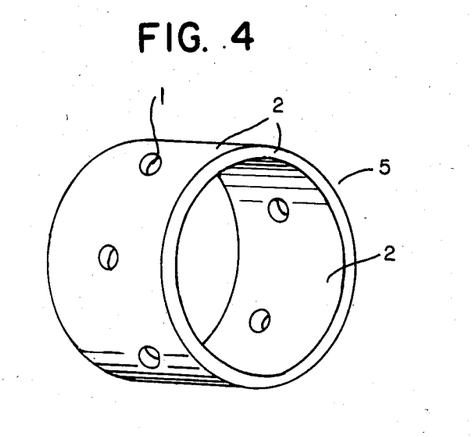
FIGS. 4 and 5 illustrate other forms of the devices of this invention.

FIG. 4 shows a perspective view of a ring-shaped device 5 of this invention, the edges of which are coated. Devices of this form are useful for intravaginal release of drugs.

Figure 5:
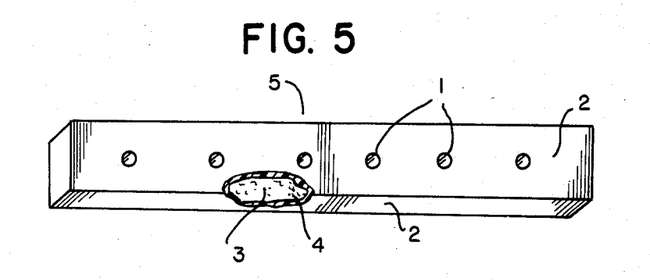

FIG. 5 represents a further embodiment of the rectangular device of FIG. 1 and is further evidence of the non-limiting shapes and sizes possible for the devices of this invention.

Figure 6:
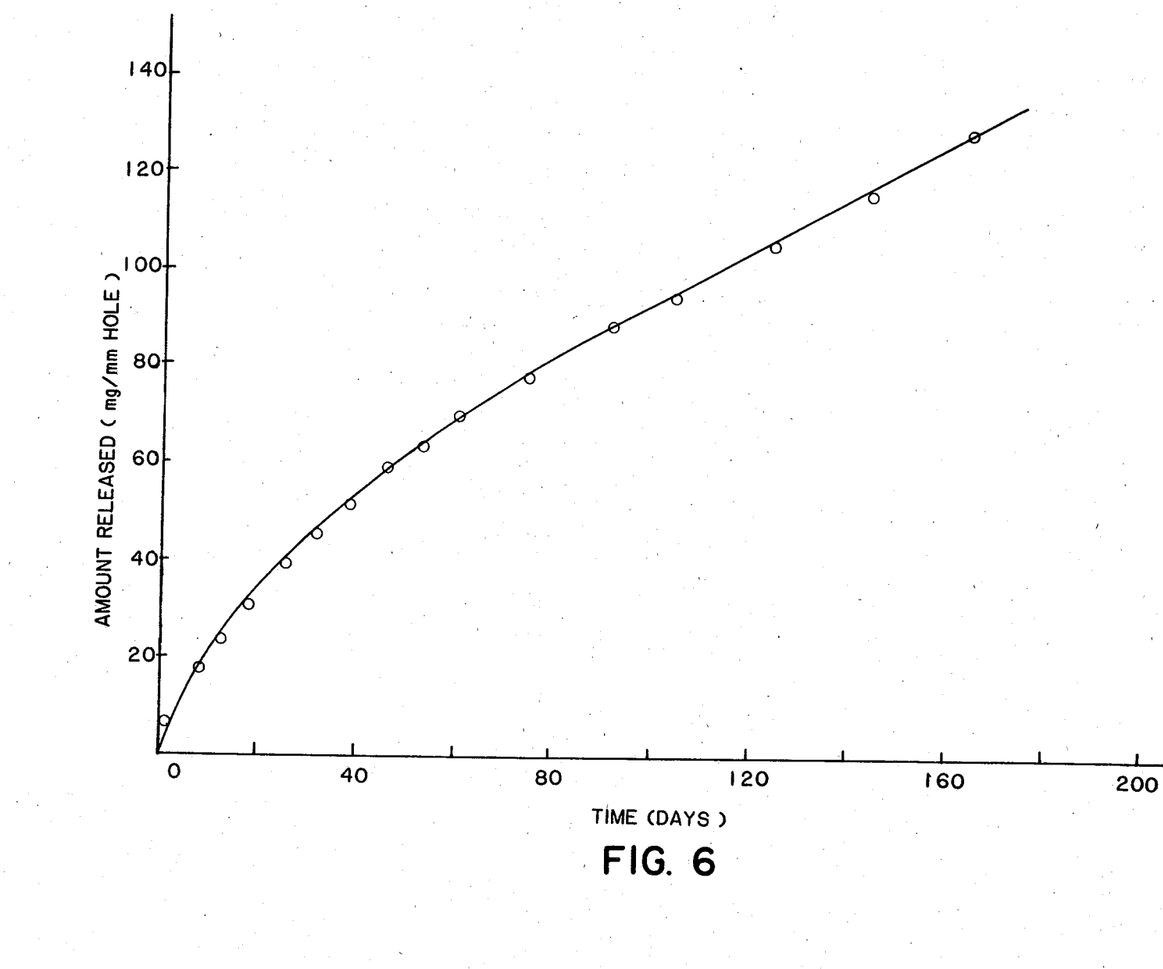
FIG. 6 presents the time-release curve for the Example 1 device and FIG. 7 the macroperforation pattern of the Example 7 device.

FIG. 6 shows the time-release curve for the device of Example 1.

Figure 7:
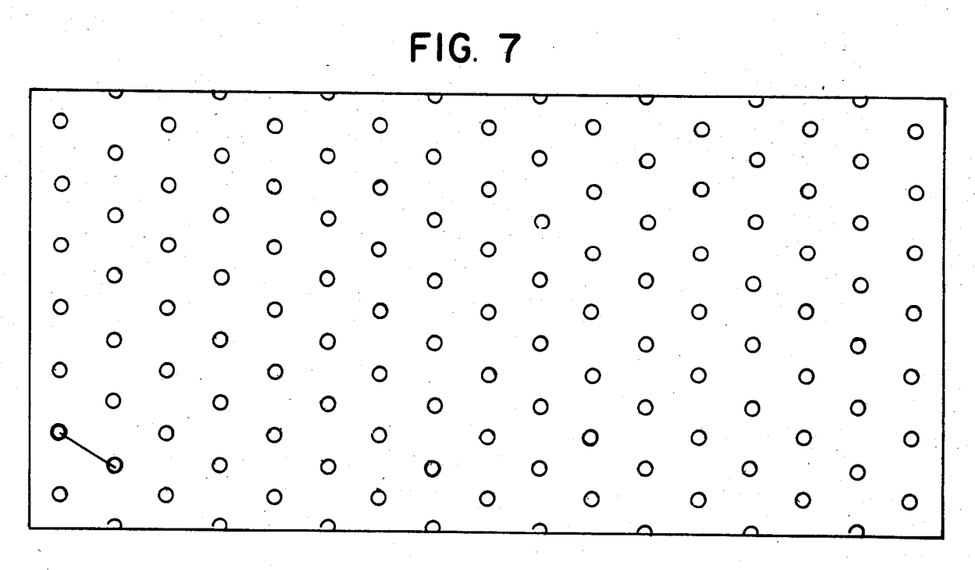

FIG. 7 illustrates the macroperforation pattern of devices of Example 7.

DETAILED DESCRIPTION OF THE INVENTION

The devices of this invention offer advantages over the controlled release devices previously available, particularly over the monolithic devices of the art. One advantage is the relative ease of manufacture of the devices of this invention. Other advantages are the nearly constant (zero order) rate of drug release over a prolonged period, and their physical stability under actual conditions of use. These advantages, along with others which will become apparent to one skilled in the art, render the devices of this invention the only practial non-reservoir type devices which are especially valuable for field use in ruminants.

The laminates of this invention can comprise a three layer (sandwich-type) laminate comprising a core sheet containing one or more active agents, said core sheet sandwiched between two coextensive inert polymeric films which are substantially impermeable to the use environment and to said agent. The edges of the laminate may be uncoated or coated. The laminates can also comprise two or more active agent-containing core sheets, each core sheet being sandwiched between coextensive inert and impermeable polymeric films so as to provide alternating layers of film and core sheet. The edges of the laminate are uncoated in one embodiment of this invention. Alternatively, and preferably, a further embodiment comprises laminates in which the edges are coated; i.e., there are no exposed edge surfaces.

The laminates of this invention, whether they comprise one or more than one core sheet and whether the edges thereof are exposed or unexposed are characterized by said core sheet comprising at least one active agent, including dispersions and solutions of active agent, homogeneously dispersed therein when a constant release rate, as opposed to a pulsed release rate, is desired; and at least one macro-hole extending through said core sheet and through the films coextensive therewith, the size, number and arrangement of said macroperforations in relation to the thickness of said core sheet being selected to expose sufficient interior edge area of said sheet to the use environment as to afford the desired release rate.

Devices of this invention which are comprised of two or more core sheets are especially valuable for controlled release of two or more active agents to an ambient environment. The fact that the properties of the individual active agents (e.g. solubility, vaporizability, potency, etc.) will differ is compensated for by incorporating, for example, into the core sheet containing the more potent active agent a suitable diluent or filler (e.g. porosigen) in sufficient amount to moderate the release rate of said agent. Of course, the two or more active agents must be compatible with one another in the use environment.

In devices of this invention comprising two or more active agent-containing core sheets, said sheets need not be separated from each other by impermeable polymeric films but can be in contact with each other. While such construction tends to reduce the overall thickness of a given device, the favored devices of this invention employ coextensive inert, impermeable polymeric films between two or more core sheets. This latter construction simplifies calculation of in vitro release rates since the active agent is exposed to the ambient environment only from the direction of the advancing solvent boundary at the surface of the cylinder.

A necessary requirement as regards the coextensive polymeric films is that they be substantially impermeable to the active agent in the core sheet. However, the core sheet need not be impermeable to the active agent as is the situation wherein the active agent is dissolved in the core sheet. However, for many uses of the devices of this invention the core sheet can comprise a polymeric material which is substantially impermeable to the active agent.

The film and core sheets can be, but need not be, made of the same polymeric material. Suitable polymeric materials are those which are substantially inert to the ambient environment; i.e., do not react chemically with any active agent which might be dispersed or dissolved within them, or with their environment, and, as regards said film, are substantially impermeable to the ambient environment. Additionally, for certain configurations of the devices of this invention, especially those having variable geometry; i.e., have one configuration when not in use and assume another configuration in the use environment, flexibility and resiliency are desirable and advantageous properties for said polymeric materials. Representative polymers fulfilling these criteria are ethylene vinylacetate copolymers which may be partially or completely hydrolyzed, poly(ethylene), poly(propylene), poly(vinyl chloride) vinylidene chloride-acrylonitrile polymers; copolymers of vinyl chloride with vinyl acetate, styrene, vinylidene chloride, dialkyl fumarate, acrylonitrile; polyacrylonitrile, poly(butylmethacrylate), poly(vinylidene chloride), polybutadiene, polyether urethane, cross-linked poly(vinylpyrrolidone), chlorinated poly(ethylene); polyacrylamide, and crosslinked partially hydrolyzed polyvinylacetate, hydroxyethyl acrylate, diethylene glycol monoacrylate, diethylene glycol monomethacrylate, 2-hydroxypropyl acrylate, 2-hydroxypropyl methacrylate, 3-hydroxypropyl acrylate, 3-hydroxypropyl methacrylate, vinylpyrrolidone, acrylamide, methacrylamide and N-propylacrylamide, silicone rubbers, especially medical grade poly(dimethylsiloxanes), poly(carbonates), silicone-poly(carbonate)copolymers; biodegradable polymers such as poly(lactic)acid, poly(glycolic)acid, poly(caprolactone) and copolymers thereof; and others known to those skilled in the art and which meet the above criteria. Ethylene vinylacetate copolymers (EVA) are preferred materials. Especially preferred are EVA containing from 10% to 60% vinyl acetate.

The polymer used for the core sheets can be a microporous polymer that is preformed and subsequently charged with the desired substance or substances. Alternatively, the core sheet is made from an imperforate polymer which, when charged with the desired substance or substances forms a microporous polymer when a device incorporating said core sheet is placed in the use environment. When the core sheet is to comprise a microporous polymer, the choice of a preformed microporous polymer or one formed in situ is determined in large part upon the amount of and distribution of the active agent present in the core sheet. Sufficient agent must be present for in situ formation of a microporous core sheet as will give rise to continuous formation of interconnected paths, channels and micropores with development of the desired microporosity when the device is in use.

An alternative, and preferred, method for in situ formation of a microporous core sheet comprises the use of a suitable porosity enhancing agent, a porosigen, in admixture with the desired active agent to be released. Said porosigens can be biodegradable, volatile or water soluble. They must be removable under the conditions of use of the devices of this invention and, of course, non-toxic under said use. Said porosigens have been referred to in the literature as modifying agents (U.S. Pat. No. 3,538,214) and as fillers (U.S. Pat. No. 4,228,149). They may also be referred to as diluents. The term "porosigen" as used herein is intended to embrace the aforementioned terms. The use of a porosigen is advantageous in instances wherein the amount of active agent contained within the core sheet is insufficient to give rise to contact between individual particles of said agent and thus prevents formation of interconnected pathways and channels (continuous micropores) when a device of this invention is in use.

The choice of porosigen depends upon the active agent in the core sheet and the use environment. Said porosigen must be compatible; i.e., not react with the agent or the environment to produce a reaction product having undesirable properties. It must be removable under the conditions of use and non-toxic or non-harmful. Favored porosigens for use in devices scheduled for use in an aqueous environment are starch, lactose, inorganic salts such as carbonates, bicarbonates, sulfates, nitrates, phosphates of the alkali metal, alkaline earth metal, ammonium, and buffering agents. Other porosigens are disclosed in the art cited herein and are incorporated herein by reference. The expression active agent as used herein applies broadly to include any substance, solid, liquid or gaseous, which can be released to a use environment to produce a beneficial effect. This includes anti-oxidants, air purifiers, pesticides, fungicides, insecticides, germicides, herbicides, perservatives, rodenticides, disinfectants, sterilization agents, foods, food supplements, drugs, nutrients, vitamins, fertility promoters, fertility inhibitors, growth promotants, trace minerals, perfumes, pheromones, chemicals released to control the rate of various reactions, and other substances that benefit the environment of use. The active agent can be organic or inorganic but must be sufficiently soluble in the release environment when said environment is a liquid environment, or sufficiently volatile when said environment is a gaseous environment, that devices of practical size can release said agent in sufficient quantity to produce the desired effect.

The term "drug" includes any physiologically or pharmacologically active agent that produces a beneficial effect in the release environment, including biological environment. The term "biological environment" includes mammals, primates, humans, animals (domestic, household, zoo, sport and laboratory), birds, reptiles and fish. Representative of drugs are those substances which exhibit antiparastic, antibiotic, antimicrobial, anti-inflammatory, analgesic, antiparkinson, anti-spasmotic, anthelmintic, antineoplastic, diuretic, hypoglycemic, anesthetic, hormonal, estrogenic, progestational steroids, prostaglandins, sedatives, hypnotics, narcotics, tranquilizers, anticonvulsants, muscle relaxants, cardiovascular agents and electrolytic behavior. The required doses for such drugs are known in the literature.

The macroperforations in the devices of this invention, together with the impermeable coating on the device surface, provide interior edges for release of active agent when the devices are placed in the use environment. These macroperforations are preferably cylindrical in shape and from 0.5–10 mm in diameter, but could assume other geometric forms such as ovals, triangles, squares, pentagons, hexagons, etc.

For a given core sheet, the dimensions of macroperforations other than the cylindrical; i.e., those wherein the surface openings are circular, should be such that the perimeter of the macroperforation at the surface of the opening approximate as closely as possible the circumference of circular openings of from 0.5–10 mm diameter. Circular macroperforations, actually cylinders when considering the overall shape through the core sheet, most nearly attain zero order release. The closer to a circle the macroperforation is, the closer it approximates zero order release.

The rate of active agent release from the macroperforations is dependent upon a number of factors (see above equations) including the effective surface area at the receding agent boundary, the length of the channel from the receding agent boundary to the interior edge of the macroperforation, the initial active agent load in the device, the diffusion coefficient for said agent in the use environment and/or core sheet, the solubility of the agent in the use environment and/or core sheet, and the number and shape of the macroperforations. Over time, all of the above factors except the first two should be constant. Thus, the variations in the release rate over time will depend upon the relative changes in these two factors. With most other devices wherein active agent release occurs from a surface which is either planar or convex, the release rate will always dramatically decrease over time due to the increase in the diffusional distance and the decrease in the area at the receding active agent boundary. In the present invention, the macroperforations are designed such that active agent release occurs from a concave surface so that the surface area at the receding drug boundary increases over time. This increasing surface area leads to an increasing release rate which partially offsets the effects due to increasing diffusional distances. Overall release is nearly zero order following an initial burst of the agent. The precise variation depends upon the size and shape of the macroperforations. The smaller the diameter of the macroperforations, and the more circular their shape, the more linear the release rate over time.

The devices of this invention can be used to release a given active agent at essentially zero order rate at one level for a certain time and then to release it at a greater or lesser level, again at essentially zero order rate, for a further period of time. A convenient way of accomplishing such a release pattern comprises incorporating the active agent and porosigen, or porosigen plus active agent, in concentric patterns within the core sheet. Proper placement of macroperforations then allows one to achieve a pulsed release of active agent.

Other methods can, of course, be used to achieve a pulsed release of active agent. In addition to the use of a variable concentration of active agent within the core sheet, as described above, variable thickness of the layer of active agent within the core sheet is a practical way of realizing pulsed release. Further, the core sheet can, for example, have grooves of varying width and depth, said groves being filled with active agent.

Devices of this invention having active agent-containing core sheets constructed as described above, are useful for essentially zero order release of more than one active agent as those skilled in the art will recognize.

Still further, when microporous EVA is used for the core sheet, advantage can be taken of the fact that high temperature reduces its tortuosity. Thus, certain portions of an active agent-containing microporous EVA core sheet can be heated so as to reduce the tortuosity of the micropores in said portions resulting in an increase in the rate of release of active agent therefrom. Proper placement of the number and size of the macroperforations affords a change in release rate of active agent from a device having such a core sheet.

Asymmetrically placed macroperforations can also be used in devices of this invention. They are especially useful in situations wherein a biphasic release rate of active agent is desired. In such devices an initial high release rate followed by a reduced but constant zero order release rate occurs and is followed by a second reduced release rate at near constant level.

Favored devices of this invention have macroperforations symmetrically or substantially symmetrically, rather than randomly, placed through both outer lamina and through the core lamina. In such embodiments of this invention, the macroperforations, preferably circular, penetrate all laminae through the smallest dimension thereof. The macroperforations can vary in diameter from 0.5 to 10 mm. Preferred devices have macroperforations of from 2 to 5 mm diameter since, when using a water soluble active agent, for example, a salt of morantel, as the agent to be released over a prolonged period of time, said diameters most closely afford essentially zero order release rate over an extended time.

For a given type device (three-layer laminate having exposed or unexposed edges) of this invention, the rate of release of a given active agent is a function of the number and size, e.g., diameter, of the macroperforations as well as of their design, i.e., symmetrical versus non-symmetrical.

For a given size device and a given water soluble agent, the release rate increases with increase in diameter and/or number of the macroperforations. The number and diameter of the macroperforations required in a given device depend upon the agent, the rate and duration of release desired and are determined by experiment or by means of the above equations.

The invention also provides methodology for making devices of this invention. In the case of devices comprising at least one core sheet, said core sheet comprising a substance dispersed therein, said core sheet being sandwiched between coextensive films of inert polymer, a convenient method comprises blending said substance into the softened, pre-formed polymer of said core sheet by known methods until a homogeneous mass is obtained. Said mass is then rolled into sheets of the desired thickness and of approximate width of the device desired, then sandwiched between said films of inert polymer and laminated or bonded thereto, desirably by applying pressure and heat sufficient to achieve bonding but insufficient to destroy said substance and said core sheet and film. The laminate is then cut to the desired dimensions. Before or after cutting of the laminate, perforations of the desired size and arrangement are made therein by known techniques. Porosigens, if used, are blended into the core sheet along with the desired substance.

While the favored method of bonding the core sheet and said coextensive films of inert polymer is by means of pressure and heat, it may be necessary, as when the active agent is volatile or heat sensitive, or at least more convenient, in certain instances to use a binder. The particular technique used depends upon the polymers used for the core sheet and the coextensive films and the nature of the substance in the core sheet. The binder used must, of course, be inert and compatible with the polymers used in the device, the substance within the core sheet and the use environment. Suitable binders are disclosed in Encyclopedia of Polymer Science and Technology, John Wiley & Sons, 8, 1968.

When the active agent is a solid substance which vaporizes over a period of time, e.g., certain insecticides, the use of heat in the bonding process is, of course, detrimental. In such instances, bonding is achieved by use of a binder. Similar technique is used when the active agent is a liquid.

When the active agent is a liquid, it is preferred to use a preformed microporous polymer for the core sheet. Said sheet is precharged with the liquid active agent in a known manner as, for example, by immersing the microporous in said liquid active agent or in a solution of said liquid active agent of known concentration followed, in the second instance, by evaporation of the solvent to leave the micropores charged with liquid active agent.

The controlled release devices of this invention can be used for a variety of purposes and situations wherein prolonged controlled release of active agents, including drugs, is desirable. They can be used for administering and for providing said agents at sites near to or remote from the point of application of the device. They can be positioned by appropriate means in suitable locations within the animal body where they are in contact with body fluids, e.g., the stomach of farm animals, especially the rumeno-reticular sac of ruminants; or on the animal body, e.g., flea collars, ear tags. Still other uses for the controlled release systems and devices of this invention occur in agriculture for administration of fertilizers, herbicides, rodenticides, pheromones, sex sterilants and pesticides; in pisciculture including aquariums and fish ponds; in drainage ditches, canals and tanks as for controlled release of algicides, biocides, disinfectants, plant growth inhibitors and promoters; and in water supplies especially for animals and poultry in need of drugs for therapeutic or prophylactic treatment.

The amount of active agent dispersed in the core sheet can vary over wide limits depending upon a variety of factors such as the amount of said agent to be delivered to an ambient environment, the time over which said agent is to be delivered, the presence or absence of a porosigen, the number and size of the macroperforations in the device, the nature of said agent and said environment and, in the case of liquid environments, the solubility of said agent in said environment.

The amount of a given agent which must be used in a device of this invention to achieve a given release rate, or determination of the release rate of a given device of this invention, is determined by in vitro tests as those skilled in the art will recognize. In general, such tests involve placing the device in question in an environment approximating the ambient environment of ultimate use intended for said device, and measuring by appropriate methodology known to those skilled in the art the amount of said agent released to said environment over a given period of time and/or by determining the amount of said agent remaining in the device after a given period of time.

In the case of a highly preferred device of this invention intended for delivery of an anthelmintic, especially morantel or a salt thereof, to the rumeno-reticular sac of a rumen, the amount of morantel (active agent) homogeneously dispersed throughout the core sheet can range from 10% to 75% by weight of said sheet. When the core sheet comprises morantel or a salt thereof dispersed in EVA, amounts greater than 75% by weight of the core sheet tend to reduce the flexibility of said sheet.

The devices of this invention can be of fixed or variable geometry. Fixed geometry devices; i.e, those which do not change their configuration in the use environment, are of value as, for example, implants, suppositories, ocular inserts, transdermal release reservoirs, vaginal inserts, ear tags for animals, dog collars, releasers of insecticides, pheromones, larvicides, molluscicides, water purification chemicals, biocides, perfumes and antibiotics; and other uses as mentioned above.

Variable geometry devices; i.e., those which undergo a change in configuration when placed in the intended use environment, are of particular value for use in environmental situations in which a controlled release device is subject to expulsion or removal before it has completed its intended task. Such situations occur, for example, in the rumeno-reticular sac of ruminant animals such as cattle and sheep. Orally administered devices must not exceed certain size and configuration for successful and convenient administration to a ruminant. However, to avoid their regurgitation by the ruminant they must be properly weighted or be of such a configuration as to prevent or at least minimize their regurgitation. Obviously, the latter property requires a device which permits convenient per os administration but which, in the rumen environment, undergoes a change in configuration thus preventing regurgitation.

The highly favored devices of this invention, especially those intended for oral administration of active agents, such as anthelmintics and growth promotants to ruminants, are of variable geometry. The preferred devices are the three layer (sandwich) laminates comprising a single core sheet and two outer films, said devices having variable geometry. Among said devices particular preference is given to those having no exposed core sheet edges. In the open configuration in the use environment, the most preferred devices are rectangular in shape so as to permit retention within the rumen. Prior to administration they are rolled into constrained cylindrical shape for easy oral administration to a ruminant. For this reason the flexibility and especially the resiliency of the core sheet are important and must not be destroyed or reduced to a level at which they fail to restore the cylinder to a substantially rectangular shape, or at least to unroll the cylinder sufficiently so as to permit retention of the device in the rumeno-reticular sac (rumen) of a ruminant.

In the case of a highly preferred device of this invention intended for delivery of an anthelmintic, especially morantel or an acid salt thereof, e.g. citrate or tartrate to the rumeno-reticular sac of a ruminant, the amount of morantel, calculated as acid salt, in the core sheet is generally from 10% to 75% by weight of said sheet. The morantel or salt thereof is finely divided prior to being dispersed in the core sheet to enable maximum dispersion and maximum homogeneity of drug therein. The above mentioned amounts of morantel insure that contact between individual particles is maintained so that when the device is placed in operation in a liquid environment, e.g. rumen of a ruminant, diffusion of morantel in said environment forms interconnected paths affording continuous release of said morantel.

For administration to a ruminant the devices are rolled so as to provide cylinders the height of which equals the shorter dimension; i.e., the width, of the device in the open configuration. The cylinders are, for ease of administration, constrained in said configuration by suitable constraining means, e.g. biodegradable string, tape or glue, water soluble adhesive, paper or gelatin capsule.

The dimensions of the preferred devices of this invention which are intended for per os administration of morantel or other substances to ruminants are not critical. As those skilled in the art will recognize the dimensions will depend in part upon the particular species of ruminant being treated.

In general, for bovines, the overall practical dimensions of the devices prior to their being rolled and constrained into cylinders for oral administration to said bovines are on the order of 7-15 cm long, 4-10 cm wide and overall thickness of 2-4 mm. Devices of these dimensions allow for convenient administration to bovines and appropriate loading of desired agent for effective treatment of said bovines.

The core sheet is suitably from 1.0 to 1.5 mm thick and the outer films from 0.1 to 0.75 mm thick. In general, the drug-containing core sheet is thicker than the total thickness of the outer films which, for simplicity of construction, are of equal thickness.

One of the major advantages of the device design described herein is that the thickness of these coatings need not be carefully controlled. In other laminated devices with rate limiting barriers such as those described in prior art, the coatings are the rate limiting barriers and therefore the thickness must be precisely controlled.

The devices when rolled and constrained into cylindrical form are, for convenient and practial reasons, from 2.0 to 3.0 cm in diameter for use in bovines.

For use in sheep, the herein described devices are, of course, smaller in size than are those for use in bovines. Dimensions ranging from 5-10 cm long, 3-8 cm wide and 1-3 mm thickness are suitable for sheep. Core sheet thickness can range from 0.4 to 1.5 mm and the outer films from 0.1 to 0.75 mm thickness. The diameter of the constrained forms is from about 0.8 to 1.5 cm in diameter.

The criterion for suitable active agents (drugs or chemicals) for use in the devices of this invention is that they be sufficiently soluble or volatile in the use environment to achieve a rate of release of said agent in said environment which will produce the desired result. For this reason, active agents which are acids or bases are often used in the form of a salt thereof. For the purpose of this invention a water soluble drug is one having a water solubility of 0.01% w/v or greater within the use environment.

Representative of the drugs which can be used in the devices described herein are the following: anthelmintics, including salts thereof, of morantel, pyrantel, oxantel, piperazine, diethylcarbamazine, levamisole, tetramisole, ivermectin and hygromycin B; antibacterials, including salts thereof, of tetracyclines, such as 5-oxytetracycline, tetracycline, chlorotetracyciine, doxycycline and Mannich bases thereof; beta-lactams such as sodium ampicillin, pivampicillin hydrochloride, penicillin G, cephaloridine, sodium salts of cefazolin, cefoxitin, cephalexin and other beta-lactams of established clinical utility; aminoglycosides such as neomycin, streptomycin, apramycin, macrolides such as erythromycin, oleandomycin and tylosin; antibacterial growth promotants such as bacitracin as its zinc or methylene disalicylic acid derivative, salts of avoparicin, polymyxin, lincomycin, bambermycin and efrotomycin; performance enhancing agents including estradiol, synovex, bovine growth hormone, diethylstilbestrol, zeranol; antiparasitic agents such as milbemycins and amprolium; essential minerals such as salts of magnesium, selenium, copper and cobalt; and vitamins such as thiamine hydrochloride; sulfa drugs such as sulfamethazine, molluscicides such as N-tritylmorpholine; and bloat prevention agents such as alcohol ethoxylates and poly(oxyethylene)-poly(oxypropylene)-poly(oxyethylene)-polymers, e.g. poloxalene; ionophore performance-enhancing agents such as salinomycin, monensin, narasin and lasalacid; larvicides such as 2-chloro-1-(2,4,5-trichlorophenyl)vinyldimethylphosphate; insecticides such as phosphorothioic acid 0-[4-[(dimethylamino)sulfonyl]phenyl]0,0-dimethyl ester, isopropyl 11-methoxy-3,7,11-trimethyldodecatrans-2-trans-4-dienoate and phosphoric acid 2,2-dichloroethenyl dimethyl ester; flukicides such as 2,3,5-trichloro-N-(3,5-dichloro-2-hydroxyphenyl)-6-hydroxybenzamide, 4-hydroxy-3-iodo-5-nitrobenzonitrile and N-[3-chloro-4-(4-chlorophenoxy)phenyl]-2-hydroxy-3,5-diiodobenzamide; and pheromones such as 2-decyl-3(5-methylhexyl)oxirane and (Z,E)-7,11-hexadecadien-L-ol-acetate for the control of gypsy moth and pink ballworm, respectively.

The devices of this invention are especially valuable for the control (therapeutic and prophylactic) of helminth infections in ruminants, cattle in particular. Protection of range animals becomes relatively convenient. In temperate climates, the low, early spring population of pasture larvae, the residue of the previous season's contamination, is multiplied by cycling through animals grazing thereon to produce, in the summer, a sharp increase in pasture infectivity. This condition gives rise, during the summer grazing season, to clinical parasitism and performance depression of animals grazing on said pasture.

The continuous and controlled release of anthelmintic agent; e.g. morantel, in the rumeno-reticular sac of grazing animals early in the season when pasture contamination is low, suppresses helminth development, deposition of eggs and subsequent larval contamination of pasture and thus breaks the above-mentioned cycle and keeps the pasture and animal worm burden at a low level. Parasitic infections of ruminants grazing on the same pasture land during the summer season is thus minimized. This "indirect" method of helminth control is especially attractive and valuable for calves since they are highly susceptible to helminths when first placed on pasture. Consistent use of the devices reduces the reservoir of infective helminth forms at a given location and at least minimizes the seasonal increase in pasture larvae which causes parasitic gastroenteritis and performance depression in grazing animals later in the season.

For "indirect control" of helminths the devices of this invention are administered to ruminants at a time in the epidemiological cycle of said helminths when pasture contamination by infective larval stages of said helminths, is declining to a minimum level. In temperate zones, this time corresponds to spring turn out; that is, the first placing of the calves out to pasture. For maximum efficiency, the device is administered to the calves within seven days of turning out. In non-temperate zones of the world, e.g. semi-tropical and tropical areas, the period of lowest pasture infectivity normally occurs prior to the rainy season. Administration of the device to ruminants in such areas is desirably carried out within two to fourteen days before the start of the rainy season.

The herein-described devices also eliminate established helminth infections from ruminants and prevent establishment of worm infections during the period of heavy challenge (summer/autumn in temperate zones). This mode of use is called "direct control". Helminth control in the non-temperate zones can also be achieved by the "direct control" method. The direct method of control protects ruminants only during the period of release of the anthelmintic agent. The indirect method of helminth control protects ruminants grazing on a given pasture for the entire season because it achieves an overall significant reduction in pasture contamination. As noted, the devices described herein provide continuous release, at a controlled rate, of drugs including anthelmintics. Particularly useful for such purposes are water-soluble salts of (E)-1,4,5,6-tetrahydro-1-methyl-2-[2-(3-methyl-2-thienyl)ethenyl]pyrimidine (morantel), (E)-1,4,5,6-tetrahydro-1-methyl-2-[2-[2-thienyl)ethenyl]]pyrimidine (pyrantel) and ($\pm$)-2,3,5,6-tetrahydro-6-phenylrmidazo[2,1-b]thiazole (tetramisole) and levamisole, the L-(−)-form thereof. Representative of preferred water-soluble salts of pyrantel and morantel are the tartrate and citrate salts; and of tetramisole and levamisole, the hydrochloride salts.

The devices of this invention are orally administered to animals by, for example, a balling gun. For use in calves, the desirable average release rate of morantel (calculated as base) is of the order of 60–200 mg (of morantel base) per day for a period of about 90 days, which covers the normal maximum survival time of the spring population of larvae. Longer release periods of from 60–180 days are desirable in the direct control mode of use since the period of exposure to heavy pasture contamination is normally prolonged. Release rates of about 60–200 mg (calculated as morantel base) per day effectively control helminth infections over such release periods. For dosing larger animals, more than one device can be administered. For indirect control of helminths using salts of pyrantel or levamisole, the desirable average release rates of each (calculated as free base) are on the order of 100–400 mg, and 100–500 mg per day, respectively for about a 90 day period. For direct control, release rates of about 100–500 mg (as free base) of pyrantel and of about 100–400 mg (as free base) of levamisole per day effectively control helminth infections over the 60–180 day period of heaviest challenge.

Continuous, low-level administration of morantel by use of the herein described devices for helminth control is effective in preventing lung worm infections in said animals during the period of drug release. Further, while cattle or sheep grazing on contaminated pasture are subject to immediate reinfection by intestinal nematodes after conventional therapeutic dosing, animals receiving the devices of this invention are essentially freed of established infection and protected from reinfection over a period of 60 days or longer.

The use of the devices for control of pasture contamination, i.e. the indirect control method, is a practical and effective method of helminth control which protects ruminants, and in particular grazing ruminants, treated via this mode for the entire grazing season. The increase in daily weight gain over untreated controls over the grazing season is substantially greater than that obtained after conventional therapy.

The rate of release of drug, or other chemical, from the controlled release devices of this invention can readily be determined by those skilled in the art, for example, by transmission methods, or by sorption-desorption methods. A technique which can conveniently be used comprises placing a given device in a rapidly stirred solvent bath, the composition of which simulates the aqueous liquid containing environment in which the device is to be used. The temperature of each solution is maintained at a value approximating the average temperature of the environment in which said device will be used. Samples are withdrawn at predetermined intervals from the solvent bath and analyzed for drug concentration.

In vivo release of morantel citrate or tartrate from devices according to this invention is determined by administering the devices to, for example, normal steers or steers with rumen fistula and, after a certain period of time such as 30, 60, 90 or 120 days, removing the devices via the fistula or sacrificing the animals and recovering the devices to determine the residual morantel citrate or tartrate within the device. Tests of this sort have shown that the rate of release of morantel citrate or tartrate in vivo is approximately 1.0 to 1.5 times that of the in vitro release rate.

The following examples are merely illustrative of the present invention. They are not to be construed as limiting the scope of this invention, many variations of which are possible as those skilled in the art will recognize.

EXAMPLE 1

A device of this invention comprising a concentric laminated device having morantel citrate as the drug and laminae of EVA was prepared as follows.

A sheet containing 60% morantel citrate and 40% EVA (Type MU-760 having 19% vinyl acetate content, available from U.S.I. Chemicals Co., 99 Park Ave., New York, N.Y. 10016) was prepared by dry blending 18.001 kg morantel citrate and 12.000 kg EVA in a 55 gallon (208 liter) fiber drum on a drum roller for 30 minutes. It was then milled at high speed to produce a mixture which passed through a 0.033 inch (0.0838 cm) screen and then drum rolled for another 30 minutes.

The resulting mixture was extruded on a 1¼ inch (3.75 cm) single screw extruder with three heating zones and a 24:1 l:d general purpose screw. The three heating zones of the extruder barrel were set to 88°, 102° and 107° C. and the screw was operated at 79 rpm. The die was a 6 inch (15.24 cm) adjustable sheet die opened to 0.110 inch (0.279 cm) and with temperature set to 88° C. The extruded sheet was passed through a three roll take-up with chilled rolls and collected.

Rectangular pieces (4"×7" 10.16 cm×17.78 cm) were cut from the thus-prepared sheet and each was pressed for 15 seconds at a pressure of 1500 pounds (680 kg) and 110° C. between platens 0.065 inch (1.651 mm) apart and then retrimmed to 4"×7" (10.16 cm×17.78 cm).

Three such sheets of core lamina were dipped into a solution of EVA (Type MU-760), 100 g/liter of toluene, to coat approximately 60% of the surface and hung in a dark cupboard to dry. After about two hours, the remaining surface was similarly treated. The devices were further dried overnight in a 60° C. oven, then weighed and their thickness measured. The devices were coated twice more with the EVA-toluene solution as described above to provide a triple coat of EVA over all surfaces.

Forty 4 mm diameter holes were punched through each of the above prepared devices in a symmetrical pattern: five rows of eight holes each.

Pertinent data on these devices are provided below.

| No. | Core Thickness (mm) | Core Weight (g) | Morantel Citrate (g) |
| --- | --- | --- | --- |
| 1 | 1.65 | 32.075 | 19.245 |
| 2 | 1.57 | 29.347 | 17.608 |
| 3 | 1.45 | 27.248 | 16.349 |

EXAMPLE 2

The in vitro release of morantel citrate by the thrice dipped concentric laminates of Example 1 was determined in the following manner.

A device of this invention containing morantel citrate was placed into a two-liter conical flask which was protected from light because of the photosensitivity of morantel citrate, 1700 ml of 0.1 M phosphate buffer (pH 6.5–6.6) added, and the temperature of the flask and contents maintained at 22° C. The flask containing the device was shaken at about 85 excursions of about 3 inches (7.62 cm) per minute and 5 ml samples were withdrawn periodically. The volume of the withdrawn sample was replaced with an equivalent volume of phosphate buffer and shaking of the flask continued. The concentration of morantel in the samples was determined spectrophotometrically by measuring the absorbance of the sample at 318 nm when read against fresh pH 6.5–6.6 phosphate buffer.

| Days in vitro | Accumulated Morantel Citrate (mg) | | |
| --- | --- | --- | --- |
| | 1 | 2 | 3 |
| 0.03 | 28.02 | 21.96 | 25.03 |
| 0.13 | 72.44 | 54.36 | 60.04 |
| 0.25 | 145.4 | 109.6 | 122.9 |
| 0.92 | 326.5 | 260.8 | 253.4 |
| 1.25 | 407.0 | 314.6 | 291.5 |
| 2.08 | 560.7 | 447.3 | 434.1 |
| 6.08 | 1114 | 905.3 | 829.0 |
| 8.12 | 1346 | 1160 | 1013 |
| 12.0 | 1742 | 1512 | 1232 |

-continued

| Days in vitro | Accumulated Morantel Citrate (mg) | | |
|---|---|---|---|
| | 1 | 2 | 3 |
| 19.0 | 2329 | 2063 | 1694 |
| 25.0 | 2864 | 2496 | 2083 |
| 32.0 | 3292 | 2831 | 2455 |
| 39.0 | 3704 | 3181 | 2762 |
| 45.9 | 4160 | 3759 | 3128 |
| 52.9 | 4448 | 4135 | 3475 |
| 61.1 | 4687 | 4495 | 3793 |
| 76.1 | 5083 | 5145 | 4403 |
| 91.9 | 5659 | 5787 | 4953 |
| 106 | 6064 | 6188 | 5266 |
| 124 | 6695 | 6856 | 6047 |
| 145 | 7302 | 7491 | 6607 |
| 165 | 7838 | 8867 | 7242 |
| 207 | 9194 | 10301 | 8590 |
| 239 | 11247 | 10064 | terminated |
| 277 | 12015 | 11038 | |
| 314 | 13202 | 11914 | |

EXAMPLE 3

Additional laminated devices of this invention were made according to the procedure of Example 1 but using 4¼"×7" (0.80 cm×17.78 cm) rectangular pieces of core material for conversion into core lamina at a pressure of 1100–1300 pounds (499–590 kg) between platens set 0.053 inch (1.346 mm) apart, a temperature of 110° C. and a dwell time of 15–17 seconds. The resulting core lamina were then trimmed to 4"×7" (10.16 cm×17.78 cm) size prior to being dipped as described in Example 1, with the exception that the entire lamina was immersed in the EVA solution so that all the surface was coated in one dip. This dipping process was performed twice.

The in vivo release of morantel citrate by these devices was determined by administering two of said devices to each of 12 rumen cannulated cattle [approximately one year old and about 700 lbs (318 kg)], Holstein and Guernsey. The cattle were fed only corn silage supplemented with one lb (0.45 kg) per head per day of a 32% protein supplement and watered ad libitum.

The cattle were divided into four groups of three and the devices were removed from the respective groups at 3, 14, 28 and 45 days and analyzed for morantel citrate content.

In the groups from which the devices were removed after 3, 14 and 28 days, two new devices were immediately placed and removed 91, 60 and 7 days later, respectively.

| Morantel Citrate Released | Time in in vivo (days) | | | | | | |
|---|---|---|---|---|---|---|---|
| | 3 | 7 | 14 | 28 | 45 | 60 | 91 |
| % (total) | 7 | 12 | 16 | 32 | 45 | 52 | 60 |
| %/day | 2.3 | 1.3 | 0.6 | 1.1 | 0.8 | 0.5 | 0.3 |
| gm (total) | 1.34 | 2.29 | 3.06 | 6.11 | 8.60 | 9.93 | 11.46 |
| gm/day | 0.45 | 0.24 | 0.11 | 0.22 | 0.15 | 0.09 | 0.05 | mean amount morantel citrate per device 19.10 g
mean thickness of core section 0.041 inch (1.04 mm)

EXAMPLE 4

Three layer laminates are prepared according to the procedure of Example 3 but using the following drugs in place of morantel citrate. The percentage values after each drug indicate the amount of said drug in the core lamina.

morantel tartrate (60%)
pyrantel citrate (75%)
pyrantel hydrochloride (65%)
tetramisole hydrochloride (50%)
levamisole hydrochloride (50%)
Ivermectin (30%)
diethylcarbamazine citrate (60%)
morantel citrate (10%, 30%)
hygromycin B (30%)
doxycycline hyclate (30%)
erythromycin hydrochloride (20%)
thiamine hydrochloride (10%)
oxytetracycline hydrochloride (50%)
ampicillin sodium salt (45%)
neomycin complex (55%)
oleandomycin hydrochloride (30%)
lincomycin hydrochloride (60%)
tylosin hydrochloride (60%)
amprolium hydrochloride (70%)
N-tritylmorpholine (50%)
salinomycin (50%)

Each of the luminates thus prepared releases the particular drug to the in vitro environment of Example 2 over a prolonged period of time at substantially zero order rate.

EXAMPLE 5

Devices prepared according to the procedure of Example 4 are dipped into EVA-toluene as described in Example 1 to provide laminates having coated edges.

The laminates so produced release their particular drug to the aqueous environment of Example 2 over an extended period of time at nearly constant rate.

EXAMPLE 6

The procedure of Example 3 is repeated except that the number and diameter of the macroperforations in the devices so produced is varied:

| Device No. | Macroperforations | |
|---|---|---|
| | No. | Diameter (mm) |
| 1 | 40 | 2 |
| 2 | 10 | 10 |
| 3 | 100 | 1 |
| 4 | 20 | 4 |
| 5 | 100 | 0.5 |
| 6 | 40 | 5 |
| 7 | 50 | 50 |
| 8 | 25 | 7.5 |
| 9 | 60 | 3 |
| 10 | 40 | 5 |

Each of said devices provides prolonged release of morantel citrate in vitro and in vivo at nearly constant rate.

EXAMPLE 7

Additional devices of this invention were made according to the procedure of Example 1, but using an initial blend of 17,000 kg of morantel citrate and 11,325 kg of EVA; extruder heating zones set to 88°, 102° and 102° C.; a screw speed of 60 rpm and a die opening of 0.106 inch (0.269 cm). The blend was fed into the extruder using a crammer feeder.

Rectangular pieces 7.4 by 3.5 inches (18.80 by 8.89 cm) were cut from the sheet, dipped twice in an EVA toluene solution as described in Example 3. After the coated pieces were dried overnight in the hood, holes 2.7 mm in diameter were punched through each of the devices in the pattern shown in FIG. 7 using a pneumatically driven single punch apparatus.

Pertinent data on the devices tested in vitro are provided below:

| No. | Core wt (g) | Morantel citrate (g) |
| --- | --- | --- |
| 1 | 39.73 | 23.84 |
| 2 | 40.18 | 24.11 |
| 3 | 40.76 | 24.46 |

Mean core thickness 0.093 inch (0.236 cm)

The in vitro release of morantel citrate by the devices prepared in this example were determined in the following manner:

A device of the invention was placed in a 750 ml brown glass bottle with 550 ml of 0.1 M phosphate buffer (pH 6.5–6.6). The bottles were placed in a thermostatted shaker bath maintained at 37° C. and shaken at about 60 excursions of about 3 inches (7.6 cm) per minute. Samples were withdrawn periodically and the volume of the withdrawn sample replaced with an equivalent volume of phosphate buffer and the shaking continued. The concentration of morantel in the samples was determined spectrophotometrically by measuring the absorbance at 318 nm when read against fresh pH 6.5–6.6 phosphate buffer.

Release of the morantel citrate was as follows:

| Days in vitro | Accumulated morantel citrate (mg) | | |
| --- | --- | --- | --- |
| | 1 | 2 | 3 |
| 1.3 | 728.3 | 730.0 | 102.8 |
| 5.1 | 271.0 | 275.9 | 242.4 |
| 8.1 | 372.9 | 371.6 | 354.1 |
| 16.0 | 627.3 | 635.8 | 586.3 |
| 22.1 | 790.4 | 778.0 | 705.5 |
| 40.0 | 1186.0 | 1145.0 | 1094.0 |
| 70.0 | 1810.0 | 1752.0 | 1627.0 |

EXAMPLE 8

Morantel tartrate and EVA (same as used in Example 1) were mixed via a blend/mill/blend operation using a drum roller and Fitzpatrick D mill with number 2 plate at medium speed and knives forward to obtain a blend containing 50/50 (w/w) blend of the materials. This blend was compounded into a sheet using a Banbury mixer and then dried into small particles for extrusion. The material was extruded using 88/96/99° C. as the zone temperatures and 105° C. as its die temperature. The screw speed was 40 RPM. The resultant sheet was approximately 0.060 inches (0.152 cm) thick and 6 inches (15.24 cm) wide. The extruded material was cut into sheets 8.15 inches (20.70 cm) long and 3.72 inches (9.45 cm) wide and dip-coated three times in a 10% EVA solution in toluene and dried at 50° C. The mean value of the initial drug load for this device was 11.27 gm. Ninety 2.7 mm diameter holes were symmetrically punched through each sheet.

The in vitro release rate of said sheets was determined according to the procedure of Example 2.

| Days in vitro | Mean gms. Morantel (as Base) Released |
| --- | --- |
| 7 | 1.12 + 5.6% |
| 14 | 1.88 + 5.1% |
| 21 | 2.72 + 5.0% |
| 27 | 3.40 + 4.6% |

The in vivo release rate, determined according to the procedure of Example 3, is presented below:

| Days in vivo | Mean gms. Morantel (as Base) Released |
| --- | --- |
| 15 | 2.89 |
| 30 | 5.46 |
| 45 | 7.38 |
| 60 | 9.02 |
| 75 | 10.80 |
| 90 | 10.90 |

EXAMPLE 9

Porosigen Containing Device

A device containing 50% EVA, 49.9% lactose and 0.1% (w/w/estradiol was prepared by blending the ingredients in a polyethylene bag for 30 minutes. The resulting blend was extruded on the machine described in Example 1 with the three heating zones set at 93/99/110° C. and 99° C. as its die temperature. The screw was operated at 40 RPM and the take-up roll at 0.93 RPM.

The extruded sheet was 0.075 inches (0.191 cm) thick and approximately 6 inches (15.24 cm) wide. Rectangular pieces 5×10 inches (12.70×25.40 cm) were cut from the extruded sheet and film coated on both sides with an EVA/polyethylene film 0.0025 inches (0.00635 cm) thick using a heated Carver press. Each sheet was punctured with two hundred 2.5 mm diameter holes.

The release rate was determined by high performance liquid chromatography using a $C_{18}$ reversed phase column and methanol:water (80:20) as the mobile phase.

The devices (perforated sheets) were placed in an aqueous solution of 0.5% sodium lauryl suflate and the solution continuously shaken in a bath maintained at 38° C. The concentration of drug was always less than 10% of the saturation solubility of the drug in the dissolution medium.

| Porosigen Containing Device | |
| --- | --- |
| Days in vitro | Milligrams Estradiol Released |
| 1 | 0.60 |
| 2 | 1.16 |
| 4 | 2.07 |
| 6 | 3.13 |
| 8 | 3.87 |
| 10 | 4.41 |
| 12 | 4.90 |
| 14 | 5.39 |
| 16 | 5.77 |
| 18 | 6.11 |
| 20 | 6.45 |
| 22 | 6.77 |
| 24 | 7.12 |
| 26 | 7.47 |
| 30 | 8.46 |

EXAMPLE 10

Fast Releasing Ampicillin Device

A mixture of 30.34 g. of EVA (same as used in Example 1) and 45.08 g. of ampicillin sodium was blended in a bottle for 30 minutes. The mixture was placed in a mold made of an aluminum spacer and two pieces of Teflon sheets which was then heated in a Carver press at 95° C. and pressed with 3000 pounds of pressure for 2 minutes.

The mold was then cooled, and rectangular sheets of 2.5×3.5×0.098 inches (6.35×8.89×0.25 cm) were cut from the pressed material and dip-coated in 10% EVA/toluene. After drying, the sheets were laminated on both sides with an EVA/polyethylene film 0.0025 inches (0.00635 cm.) thick using a heated Carver press. Four symmetrically placed holes 2.5 mm in diameter were punched through each sheet.

The individual sheets were placed in water at 4° C. with constant stirring and the release determined over a seven day period by spectrophotometric assay of the solutions at 260 nm.

| Fast Releasing Ampicillin Device | |
| --- | --- |
| Hours in vitro | Milligrams Ampicillin Released |
| 2 | 36.4 |
| 3.5 | 51.5 |
| 9 | 87.4 |
| 20 | 142 |
| 24 | 157 |
| 27 | 173 |
| 44 | 243 |
| 48 | 253 |
| 52 | 261 |
| 68 | 319 |
| 70 | 320 |
| 72 | 329 |
| 76 | 339 |
| 92 | 389 |
| 96 | 400 |
| 120 | 464 |
| 144 | 527 |
| 169 | 589 |

EXAMPLE 11

Laminated Silastic Device

For a typical device, 64.63 g. of Silastic 382 Medical Grade Elastomer (Dow Corning) and 0.64 g. of beta-estradiol were mixed in a weighing dish. The mixture was stirred with a spatula for 10 minutes. The curing agent, stannous octoate (Dow Corning Catalyst M), was added dropwise to the mixture on a balance until the total amount of curing agent was approximately 0.142 g. The mixture was stirred for another 10 minutes then poured into a plastic mold with dimensions of 0.1"×4"×6" (0.254+10.16+15.24 cm). The mold containing the mixture was placed in a vacuum oven to remove air bubbles in the mixture then sealed with a plastic plate. The plate and the mold were held together with two metal plates by a number of screws. The mixture in the mold was left at 38° C. for 24 hours.

The device was taken out of the mold and laminated with EVA/polyethylene with Medical Adhesive Type A (Dow Corning) film. A second EVA/polyethylene sheet was laminated to this device using the procedure outlined in Example 9. The devices were punctured with 96 holes 0.088" (2.24 mm) in diameter. The release was done as in Example 9.

| Laminated Silastic Device | |
| --- | --- |
| Days in vitro | Milligrams Estradiol Released |
| 1 | 0.94 |
| 2 | 1.50 |
| 4 | 2.35 |
| 6 | 2.96 |
| 8 | 3.47 |
| 10 | 3.97 |
| 12 | 4.50 |
| 14 | 4.93 |
| 16 | 5.38 |
| 18 | 5.84 |
| 22 | 6.59 |
| 26 | 7.27 |

EXAMPLE 12

The procedure of Example 8 was repeated except that the extruded material was dip-coated in a 10% EVA solution in toluene then cut into sheets 8.15 inches (20.70 cm) long and 3.72 inches (9.45 cm) wide. The sheets thus produced have exposed edges. Thirty-nine 2.7 mm. diameter holes were punched through each sheet.

The in vitro release rate of said sheets was determined according to the procedure of Example 2.

| Time (days) | Mean gms. Morantel Base Released |
| --- | --- |
| 7 | 0.94 ± 13% |
| 14 | 1.43 ± 11% |
| 20 | 1.88 ± 13% |

I claim:

1. A device for controlled and prolonged release of at least one active agent to an ambient environment comprising
   at least one core sheet sandwiched between coextensive polymeric films which are substantially impermeable to said environment and to said agent,
   said core sheet comprising a mixture of said agent in a polymer matrix,
   said device having one or a plurality of macroperforations extending through said films and said core sheet,
   the diameter and arrangement of said macroperforations in relation to the thickness of said core sheet being selected to expose sufficient interior edge area of said sheet to said environment to afford the desired release rate of said agent.

2. The device of claim 1 wherein said macroperforations are symmetrically distributed over the face of said device and said core sheet comprises a homogenous mixture of active agent in the polymer matrix.

3. The device of claim 1 wherein said macroperforations are circular to afford interior edges of cylindrical configuration for exposure of said agent to said environment.

4. The device of claim 3 wherein said macroperforations are from about 0.5 to 10 mm in diameter.

5. The device of claim 1 wherein the perimeter edge of said core sheet is coated by a film substantially impermeable to said environment and to said agent.

6. The device of claim 1 wherein said agent is dissolved in said core sheet.

7. The device of claim 1 wherein said agent is dispersed in said core sheet.

8. The device of claim 1 wherein said agent is released by vaporization into a gaseous environment.

9. The device of claim 1 wherein said agent is released into a liquid environment in which said agent exhibits a finite solubility and in which said film and said core polymers are substantially insoluble.

10. The device of claim 9 wherein said agent is present at a level of from about 0.1 to 75 weight % of said core sheet.

11. The device of claim 9 wherein said core sheet contains a dispersed porosigen of finite solubility in said environment.

12. The device of claim 9 wherein said agent is characterized by finite solubility in an aqueous environment.

13. The device of claim 12 wherein said agent is a drug.

14. The device of claim 12 for oral administration to a ruminant, wherein said film and said core sheet are flexible and resilient and capable of constrainment in rolled configuration by constraining means releasable in an aqueous environment.

15. The device of claim 14 wherein said agent is an anthelmintic agent.

16. The device of claim 15 wherein said agent is a water-soluble acid addition salt of morantel, pyrantel or levamisole.

17. The device of claim 16 wherein said agent is morantel citrate.

18. The device of claim 16 wherein said agent is morantel tartrate.

19. A device for controlled and prolonged release of anthelmintic in a ruminant comprising
a resilient and flexible ethylene-vinyl acetate copolymer core sheet sandwiched between a pair of coextensive resilient films of said copolymer,
said core sheet containing from about 10 to 75% by weight of a water-soluble morantel salt dispersed therein,
said device having one or a plurality of circular macroperforations about 0.5 to 10 mm in diameter symmetrically distributed across the face of said device and extending through said films and said core sheet,
the diameter and arrangement of said macroperforations in relation to the thickness of said core sheet being selected to expose sufficient interior edge area of said sheet to afford the desired morantel release rate,
said device being capable of constrainment in rolled configuration by constraining means releasable in the rumen of an animal.

20. The device of claim 19 wherein the perimeter edge of said core sheet is sealed by a film of ethylenevinyl acetate copolymer.

21. The device of claim 19 wherein said salt is morantel citrate.

22. The device of claim 19 wherein said salt is morantel tartrate.

23. A three-layer laminate device for the controlled and continuous release of a water-soluble active agent to an aqueous liquid-containing environment over a prolonged period of time, said device comprising
(a) a core sheet comprising a water soluble active agent dispersed in an amount corresponding to from 10% to 75% by weight of said core sheet, said sheet comprising a polymeric material insoluble in said aqueous liquid-containing environment, resilient, flexible and impermeable to said agent and to said environment;
(b) said core sheet being sandwiched between two coextensive films of polymeric material which are resilient, insoluble in said aqueous liquid-containing environment, flexible and impermeable to said environment and to said agent;
(c) the thus-produced three-layer laminate having one or a plurality of macroperforations extending through said films and said core;
(d) said three-layer laminate being capable of constrainment by constraining means in a rolled-up configuration, the constraining means being operable to release the constrained laminate when said laminate is placed in an aqueous liquid-containing environment.

24. A device according to claim 23 wherein the perimeter edge of said core sheet is sealed by a polymeric material.

25. A device according to claim 23 wherein the macroperforations are from 0.5 to 10 mm in diameter.

26. A device according to claim 23 wherein the aqueous liquid-containing environment is the rumeno-reticular sac of a ruminant and the active agent is a drug.

27. A device according to claim 26 wherein the drug is an anthelmintic agent.

28. A device according to claim 27 wherein said anthelmintic agent is a water-soluble acid addition salt of morantel, pyrantel or levamisole.

29. A device according to claim 28 wherein said salt is selected from the group consisting of levamisole hydrochloride and the tartrate and citrate salts of morantel and pyrantel.

30. A device according to claim 29 wherein said salt is morantel citrate.

31. A device according to claim 30 wherein said salt is morantel tartrate.

32. A method for the control of helminthiasis in ruminant animals which comprises administering to said animals for retention in the rumeno-reticular sac, a device for the controlled and continuous administration of a water soluble salt of morantel to the aqueous liquid-containing environment in said rumeno-reticular sac over a prolonged period of time, said device comprising
(a) a core sheet comprising a water soluble salt of morantel dispersed in a sheet of ethylene vinyl acetate copolymer in an amount corresponding to from 10% to 75% by weight of said core sheet, said core sheet being insoluble in said aqueous liquid-containing environment, resilient, flexible and impermeable to said morantel salt and to said environment;
(b) said core sheet being sandwiched between two coextensive polymeric films of ethylene vinyl acetate copolymer which are insoluble in said aqueous liquid-containing environment, resilient, flexible and impermeable to said environment and to said morantel salt;
(c) the thus-produced three-layer laminate having one or a plurality of macroperforations extending through all laminae;
(d) said three-layer laminate being capable of constrainment by constraining means in a rolled-up configuration, the constraining means being operable to release the constrained laminate when said laminate is placed in said aqueous liquid-containing environment.

33. The method according to claim 32 wherein the water soluble morantel salt is morantel citrate.

34. The method according to claim 32 wherein the water soluble morantel salt is morantel tartrate.

35. A method for the control of helminthiasis in ruminant animals which comprises administering to said animals for retention in the rumeno-reticular sac, a device for the controlled and continuous administration of a water soluble salt of morantel to the aqueous liquid-containing environment in said rumeno-reticular sac over a prolonged period of time, said device comprising
   (a) a core sheet comprising a water soluble morantel salt dispersed in a sheet of ethylene vinyl acetate copolymer in an amount corresponding to from 10% to 75% by weight of said core sheet, said core sheet being insoluble in said aqueous liquid-containing environment, resilient, flexible and impermeable to said morantel salt and to said environment;
   (b) said core sheet being coated on all sides by ethylene vinyl acetate copolymer which is insoluble in said aqueous liquid-containing environment, resilient, flexible and impermeable to said environment and to said morantel salt;
   (c) the thus-produced laminate having one or a plurality of macroperforations extending through all laminae;
   (d) said laminate being capable of constrainment by constraining means in a rolled-up configuration, said constraining means being operable to release the constrained laminate when said laminate is placed in said aqueous liquid-containing environment.

36. A method according to claim 35 wherein the morantel salt is morantel citrate.

37. A method according to claim 35 wherein the morantel salt is morantel tartrate.

38. A method for the control of helminths on pasture land, the helminth larvae contamination of which is at or near a minimum level, which comprises grazing on said land ruminant animals having in their rumeno-reticular sacs, a device for the controlled and continuous administration of a water soluble salt of morantel to the aqueous liquid-containing environment in said rumeno-reticular sac over a prolonged period of time, said device comprising
   (a) a core sheet comprising a water soluble morantel salt dispersed in a sheet of ethylene vinyl acetate copolymer in an amount corresponding to from 10% to 75% by weight of said core sheet, said core sheet being insoluble in the aqueous liquid-containing environment, resilient, flexible and impermeable to said morantel salt and to said environment;
   (b) said core sheet being coated on all sides by ethylene vinyl acetate copolymer which is insoluble in said aqueous liquid-containing environment, resilient, flexible and impermeable to said environment and to said morantel salt;
   (c) the thus-produced laminate having one or a plurality of macroperforations extending through all laminae;
   (d) said laminate being capable of constrainment by constraining means in a rolled-up configuration, said constraining means being operable to release the constrained laminate when said laminate is placed in said aqueous liquid-containing environment.

* * * * *